United States Patent [19]
Pietro et al.

[11] Patent Number: 6,080,881
[45] Date of Patent: Jun. 27, 2000

[54] PROCESS FOR PREPARING 2-ACETYTHIO-3-PHENYL-PROPIONIC ACID AND THE SALTS THEREOF

[75] Inventors: Allegrini Pietro, Lonigo; Soriato Giorgio, San Martino Buon Albergo, both of Italy

[73] Assignee: Zambon Group S.p.A., Vicenza, Italy

[21] Appl. No.: 09/251,468

[22] Filed: Feb. 17, 1999

[30] Foreign Application Priority Data

Feb. 18, 1998 [IT] Italy ................................. MI98A0301

[51] Int. Cl.⁷ ................................. C07C 153/09
[52] U.S. Cl. ............................................. 558/255
[58] Field of Search ............................ 558/255

[56] References Cited

U.S. PATENT DOCUMENTS

| | | | |
|---|---|---|---|
| 4,339,600 | 7/1982 | Ondetti et al. | 562/426 |
| 5,504,080 | 4/1996 | Karanewsky | 514/214 |
| 5,508,272 | 4/1996 | Robl | 514/80 |

FOREIGN PATENT DOCUMENTS

| | | |
|---|---|---|
| 524 553 A1 | 1/1993 | European Pat. Off. . |
| 657 453 A1 | 6/1995 | European Pat. Off. . |
| 63-20363 | 2/1987 | Japan . |
| 2055814 | 7/1980 | United Kingdom . |

OTHER PUBLICATIONS

"α–Mercaptoacyl Dipeptides that Inhibit Angiotensin Converting Enzyme and Neutral Endopeptidase 24.11"; Bioorganic & Medicinal Chem. Letters; vol. 5, No. 7; pp. 735–738, 1995.

"Optimal Recognition of Neutral Endopeptidase and Angiotensin–Converting Enzyme Active Sites by Mercaptoacyl-dipeptides as a Means to Design Potent Dual Inhibitors" Pascale Coric et al.; J. Med. Chem. 1996, vol. 39, pp. 1210–1219.

"Design of Orally Active Dual Inhibitors of Neutral Endopeptidase and Angiotensin–Converting Enzyme with Long Duration of Action", Marie–Claude Fournie–Zaluski et al.; J. Med. Chem. 1996, vol. 39, pp. 2594–2608.

Synthesis of $C_2$–Symmetric HIV Protoase Inhibitors With Sulfur–Containing Control Units; Andrew Spaltenstein et al.; Tetrahedron Letters, vol. 34, No. 9, pp. 1457–1460. 1993.

"Synthesis of (Racemization Prone) Optically Active Thiols by $S_N2$ Substitution Using Cesium Thiocarboxylates";Bert Strijtveen et al.; J. Org. Chem. 1986; vol. 51; pp. 3664–3671.

*Primary Examiner*—Ardin H. Marschel
*Assistant Examiner*—Sherif Kafafi
*Attorney, Agent, or Firm*—Arent, Fox Kintner Plotkin & Kahn

[57] ABSTRACT

It is described a process for preparing 2-acetylthio-3-phenyl-propionic acid and the salts thereof starting from 2-bromo-3-phenyl-propionic acid and potassium thioacetate in an organic solvent and in the presence of a phase transfer catalyst.

13 Claims, No Drawings

PROCESS FOR PREPARING 2-ACETYTHIO-3-PHENYL-PROPIONIC ACID AND THE SALTS THEREOF

The present invention relates to a process for preparing 2-acetylthio-3-phenyl-propionic acid and the salts thereof.

2-Acetylthio-3-phenyl-propionic acid and the salts thereof are intermediates useful in the preparation of many substances, particularly in the synthesis of ACEINEP inhibitors. See, for example, the patent application EP-0 524 553 (in the name of I.N.S E.R.M.) disclosing antihypertensive acylmercaptoalkanoylpeptides, the patent U.S. Pat. No. 4,339,600 (in the name of Squibb & Sons) relating to antihypertensive mercaptoacyl amino acids, the patents U.S. Pat. No. 5,504,080 and U.S. Pat. No. 5,508,272 (both in the name of Bristol-Myers Squibb) claiming ACE/NEP inhibitors. As far as we know, one of the most common synthetic routes to 2-acetylthio-3-phenyl-propionic acid and the salts thereof starts from phenyl-alanine which is chlorinated or brominated to give the intermediate 2-bromo- or -chloro-3-phenylpropionic acid. This acid is then suitably treated to give the desired compound.

Commonly, when 2-acetylthio-3-phenyl-propionic acid is desired in (S) or (R) racemic form, the synthesis starts from (D)- or (L)-phenyl-alanine respectively which, maintaining the optical configuration, provides (R)- or (S)-2-bromo- or -chloro-3-phenylpropionic acid respectively which yields the desired product, by inverting the optical configuration.

In the just cited patent application EP-0 524 553 (R)-2-bromo-3-phenyl-propionic acid is reacted, under nitrogen, with thioacetic acid/potassium carbonate in the presence of 1M sodium hydroxide to give (S)-2-acetylthio-3-phenyl-propionic acid which is extracted in ethyl acetate with a yield of 75%.

The patent application EP-0 657 453 (in the name of Bristol-Myers Squibb) describes the synthesis of 2-acetylthio-3-phenyl-propionic acid starting from 2-bromo-3-phenylpropionic acid which is reacted with a mixture of thioacetic acid and potassium hydroxide in acetonitrile under argon at room temperature for about 6 hours overall. The oily residue is redissolved in ethyl acetate and washed with water and an aqueous solution of potassium bisulfate. After removing ethyl acetate under vacuum the resultant crude was salified with dicyclohexylamine using isopropyl ether as crystallization solvent, and optionally re-crystallyzed from ethyl acetate (yield: 78% over the crude).

The use of thioacetic acid provided for in the above said processes of the prior art yields problems from the work environment point of view because of its strong smell of hydrogen sulfide. Furthermore the isolation work-up of the product is elaborate and acetonitrile is a toxic and even expensive solvent.

Bhagwat S. S. et al., Bioorg. & Med. Chem. Letters, 5, 7, 735–8, 1995 describe in outline the synthesis of (S)-2-acetylthio-3-phenyl-propionic acid starting from (R)-2-bromo-3-phenylpropionic acid, thioacetic acid and caesium carbonate. Besides the just criticized use of thioacetic acid, this process is further affected by the disadvantage of the obliged use of dimethylformamide as reaction solvent which makes elaborate the isolation work-up of the product. Actually this article refers to Strijtveen B. and Kellogg M., J.Org.Chem., 51, 3664–3671, 1986, which, disclosing the synthesis of various optically active thiols, and particularly of (R)-2-(benzoylthio)-propionic acid, explain that caesium carbonate must be previously reacted with thioacetic acid in methanol to obtain caesium thioacetate which is the reactive species in the process in question which is just carried out in dimethylformamide. It also takes to underline that caesium carbonate is not an easily available reactant. Coric P. et al., J.Med.Chem., 39, 1210–1219, 1996, provide a general synthetic scheme for 2-acylthio-alkanoic acids, among which also 2-acetylthio-3-phenyl-propionic acid is comprised. The synthesis starts from 2-bromo-3-phenylpropionic acid (1 equivalent) which is treated with sodium thioacetate (1.5 equivalents) in dimethylformamide, first at 0° C. then at room temperature overnight. The product is extracted in ethyl acetate -md gives a yield of 62%.

Fournie-Zaluski M. -C. et al., J.Med.Chem., 39, 2594–2608, 1996, generally describe the synthesis of optically active 2-acylthio-alkanoic acids, among which 2-acetylthio-3-phenyl-propionic acid, starting from 2-bromo-3-phenyl-propionic acid (1 equivalent) which is treated with potassium thioacetate (1 equivalent) in dimethylformamide, under nitrogen at 0° C. After chromatography an oily product is obtained with a yield of 98%. Th presence of dimethylformamide makes the isolation work-up of the final product elaborate.

An alternative to the use of dimethylformamide is given by Spaltenstein A. et al., Tetrahedron Letters, 34, n.9, 1457–1460, 1993 illustrating the synthesis of 2-acetylthio-3-phenyl-propionic acid from 2-bromo-3-phenyl-propionic acid which is treated with potassium thioacetate in methanol at room temperature for 12 hours. The product yield is 90%. Also in the case of methanol the complexity of the product isolation is troublesome. As far as we know, the salts of 2-acetylthio-3-phenyl-propionic acid are poorly stable in methanol, thus it is necessary to change the solvent for isolating the product, and this clearly complicates the work-up.

It has been now surprisingly found a new synthetic method for 2-acetylthio-3-phenyl-propionic acid which is industrially applicable and advantageous.

Therefore the present invention relates to a process for preparing 2-acetylthio-3-phenyl-propionic acid starting from 2-bromo-3-phenyl-propionic acid and potassium thioacetate in an organic solvent characterized in that the reaction is carried out in the presence of a phase transfer catalyst.

Preferably, the process object of the present invention is used for preparing (S)-2-acetylthio-3-phenyl-propionic acid starting from (R)-2-bromo-3-phenyl-propionic.

As phase transfer catalyst useful for the scope of the present invention crown ethers, cryptands and ammonium and phosphonium salts are meant. Ammonium salts are the preferred catalysts of the present invention, and even more preferred are the asymmetric ammonium salts. Specific examples of asymmetric ammonium salts useful for the scope of the present invention are trioctylmethylammonium, methyltrialkyl($C_{8-10}$)ammonium, dioctadecyldimethylammoniun and tridodecylmethylammonium salts.

For practical (low toxicity) and economical reasons trioctylmethylammonium salts, marketed as ALIQUAT (Henkel Corporation), and methyltrialkyl($C_{8-10}$)ammonium salts marketed as Adogen® (Ashland Chemical Co.) are preferably used. The ALIQUAT 336® trioctylmethylammonium salts are particularly preferred.

The amount of catalyst employed for the scope of the present invention ranges from 0.05 to 5% molar, preferably from 0.3 to 1% molar with respect to 2-bromo-3-phenyl-propionic acid. As organic solvents fit for the scope of the present invention aromatic hydrocarbons, chlorinated hydrocarbons, ethers, esters, carbonates and the like are meant.

The reaction is preferably carried out in ethyl acetate or toluene.

The reaction is effected at a temperature from −10° C. to 50° C., preferably from 0° C. to 20° C. The product is washed with water and an aqueous solution of sodium thiosulfate or a hydrate derivative thereof. Among the hydrate derivatives of sodium thiosulfate the pentahydrate is the preferred one.

2-Acetylthio-3-phenyl-propionic acid may be then turned into a salt thereof by treating a solution of the acid in an organic solvent as defined above, ethyl acetate being the preferred solvent, with the due base to give a mixture from which the desired salt precipitates and is purified by common methods.

The particular and specific conditions which the synthesis object of the present invention is effected at allow the obtainment of the product with yields of about 90%, while yielding the desired optical configuration by inverting the one of the starting acid.

The presence of the phase transfer catalyst is critical. It permits to carry out the reaction under industrially acceptable conditions (i.e. industrially suitable reactants) while minimizing the isolation work-up and maintaining very profitable yields. As shown in the comparative example, the absence of the phase transfer catalyst makes the yield dramatically drop.

For better illustrating the present invention the following examples are now provided.

EXAMPLE 1

Synthesis of (S)-2-acetylthio-3-phenyl-propionic acid

In a 3 l-jacketed reactor, with mechanical stirring, refrigerator and thermometer, (R)-2-bromo-3-phenyl-propionic acid (385.8 g, 1.68 moles), ethyl acetate (1,143 ml) and ALIQUAT 336® (4.2 g, 0.01 mole) were charged at 15° C. under nitrogen flow. The mixture temperature was brought to 0° C. and potassium thioacetate (222 g, 1.944 moles) was added in two portions. The reaction temperature was kept at 15° C. for 6 hours, then the mixture was twice washed with an aqueous solution of sodium thiosulfate pentahydrate (84.6 g in 820 ml of water over-all), then twice with demineralized water (600 ml total). The phases were separated and the organic one was concentrated under vacuum in a thermostated bath at 35–40° C. The resulting organic solution was cooled and filtered over celite, then added with ethyl acetate (600 ml). On the basis of the HPLC analysis, the yield in solution was equal to 87%.

EXAMPLE 2

Synthesis of (S)-2-acetylthio-3-phenyl-propionic acid dicyclohexylamine salt

In a 3 l-jacketed reactor, with mechanical stirring, refrigerator and thermometer, crude (S)-2-acetylthio-3-phenyl-propionic acid (330.6 g 1.474 moles) in ethyl acetate prepared as described in Example 1 was charged and then, under nitrogen at 15–20° C., dicyclohexylamine (312 g, 1.721 moles in all) was dropped in 2 portions alternated by the addition of (S)-2-acetylthio-3-phenyl-propionic acid dicyclohexylamine salt (0.6 g) as crystallization primer. At the end of the addition, the mixture was heated to 55° C. for 30 minutes., then cooled to 0° C. and after 2 hours it was filtered. The resulting solid was washed with ethyl acetate (200 mlx3) at 0° C. and dried for 24 hours at 35–40° C. to give 521.4 g of (S)-2-acetylthio-3-phenyl-propionic acid dicyclohexylamine salt (yield: 76.3%).

EXAMPLE 3

Synthesis of (S)-2-acetylthio-3-phenyl-propionic acid dicyclohexylamine salt

In a 1 l-jacketed reactor, with mechanical stirring, refrigerator and thermometer, (R)-2-bromo-3-phenyl-propionic acid (138.25 g, 0.6 mole), ethyl acetate (342.3 ml) and ALIQUAT 336® (4.2 g, 0.01 mole) were charged at 15–20° C. under nitrogen flow. The mixture temperature was brought to 10° C. and potassium thioacetate (74 g, 0.648 mole) was added. The reaction temperature was kept at 15–17° C. for 5 hours, then the mixture was twice washed with an aqueous solution of sodium thiosulfate pentahydrate (20.8 g in 179.2 ml of demineralized water). The phases were separated and the organic one was concentrated under vacuum in a thermostated bath at ≦40° C. The resulting organic solution was cooled at 15–17° C. and filtered over celite, then added with ethyl acetate (270.3 ml) to yield a solution (600 ml) which was charged in a 1 l-jacketed reactor with mechanical stirring, refrigerator and thermometer. Under nitrogen at 15–20° C., dicyclohexylamine (104 g, 0.573 mole overall) was dropped in 2 portions alternated by the addition of pure (S)-2-acetylthio-3-phenyl-propionic acid dicyclohexylamine salt (0.2 g) as crystallization primer. At the end of the addition, th(mixture was kept at 15–17° C. for 30 minutes, then heated to 52–55° C. for 30 minutes, then cooled to 0° C. and after 2 hours it was filtered. The resulting solid was washed with ethyl acetate (60 mlx3) at 0° C. and dried for 24 hours under vacuum at 35–40° C. to give 182.6 g of (S)-2-acetylthio-3-phenyl-propionic acid dicyclohexylamine salt.

COMPARATIVE EXAMPLE 1

Synthesis of (S)-2-acetylthio-3-phenyl-propionic acid dicyclohexylamine salt

Example 3 was exactly repeated without the phase transfer catalyst (ALIQUAT 336®). There were obtained 173.4 g of (S)-2-acetylthio-3-phenyl-propionic acid dicyclohexylamine salt, i.e. an amount 10% lower then the one yielded in example 3.

We claim:

1. Process for preparing 2-acetylthio-3-phenyl-propionic acid starting from 2-bromo-3-phenyl-propionic acid and potassium thioacetate in an organic solvent wherein the reaction is carried out in the presence of a phase transfer catalyst.

2. Process according to claim 1 wherein (S)-2-acetylthio-3-phenyl-propionic acid is prepared starting from (R)-2-bromo-3-phenyl-propionic acid.

3. Process according to claim 1 wherein the phase transfer catalyst is selected from the group consisting of crown ethers, cryptands and ammonium and phosphonium salt.

4. Process according to claim 1 wherein the phase transfer catalyst is an ammonium salt.

5. Process according to claim 1 wherein the phase transfer catalyst is an asymmetric ammonium salt.

6. Process according to claim 5 wherein the asymmetric ammonium salt is selected from the group consisting of trioctylmethylammoniun, methyltrialkyl($C_{8-10}$)ammonium, dioctadecyldimethylammonium and tridodecylmethylammonium salts.

7. Process according to claim 5 wherein the asymmetric ammonium salt is a trioctylmethylammonium salt or a methyltrialkyl($C_{8-10}$)ammonium salt.

8. Process according to claim 5 wherein the asymmetric ammonium salt is a trioctylmethylammonium salt.

9. Process according to claim 1 wherein the amount of phase transfer catalyst is from 0.05 to 5% molar with respect to 2-bromo-3-phenyl-propionic acid.

10. Process according to claim 1 wherein the amount of phase transfer catalyst is from 0.3 to 1% molar with respect to 2-bromo-3-phenyl-propionic acid.

11. Process according to claim 1 wherein the organic solvent is selected from the group consisting of aromatic hydrocarbons, chlorinated hydrocarbons, ethers, esters, carbonates.

12. Process according to claim 1 wherein the organic solvent is selected from the group consisting of toluene and ethyl acetate.

13. Process according to claim 1 wherein the solvent is ethyl acetate.

* * * * *